(12) United States Patent
Grosser et al.

(10) Patent No.: US 10,345,271 B2
(45) Date of Patent: Jul. 9, 2019

(54) MODULAR FILM-COVERED ELASTOMERIC INSPECTION DEVICE

(71) Applicant: Spirit AeroSystems, Inc., Wichita, KS (US)

(72) Inventors: Michael R. Grosser, Serby, KS (US); Kendall Ford Koerner, Wellington, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 149 days.

(21) Appl. No.: 15/232,923

(22) Filed: Aug. 10, 2016

(65) Prior Publication Data

US 2018/0045685 A1    Feb. 15, 2018

(51) Int. Cl.
G01N 29/04     (2006.01)
G01N 29/28     (2006.01)
G01N 29/265    (2006.01)

(52) U.S. Cl.
CPC ........... *G01N 29/28* (2013.01); *G01N 29/043* (2013.01); *G01N 29/265* (2013.01); *G01N 2291/0231* (2013.01); *G01N 2291/106* (2013.01)

(58) Field of Classification Search
CPC .... G01N 29/28; G01N 29/225; G01N 29/265; G01N 29/041; G01N 29/221; G01N 29/4436
See application file for complete search history.

(56) References Cited

U.S. PATENT DOCUMENTS

| | | | | |
|---|---|---|---|---|
| 3,413,843 | A | * | 12/1968 | Kortenhoven ......... G01N 29/27 73/638 |
| 3,663,842 | A | * | 5/1972 | Miller .................... B06B 1/067 252/62 |
| 3,670,562 | A | * | 6/1972 | Muto ..................... B21B 38/00 73/634 |
| 4,073,193 | A | * | 2/1978 | Mastandrea ......... G01N 29/045 310/334 |
| 4,195,530 | A | * | 4/1980 | Ross ...................... G01N 29/26 73/638 |
| 4,297,886 | A | * | 11/1981 | Anikeev ............... G01N 29/221 73/642 |
| 4,312,230 | A | * | 1/1982 | Bricker ................. G01N 29/26 73/638 |
| 4,488,435 | A | * | 12/1984 | Kastl .................... G01N 29/265 73/618 |

(Continued)

*Primary Examiner* — Helen C Kwok
(74) *Attorney, Agent, or Firm* — Hovey Williams LLP (57) ABSTRACT

An inspection system for ultrasonic inspection of a part, such as an aircraft component. The inspection system may include one or more transducers, an acoustic coupler made of an acoustic coupling compliant solid, a low friction contact film, a location sensor, and a processor. The contact film may substantially surround the acoustic coupler or portions thereof. The transducers may transmit ultrasonic or sound waves through the acoustic coupler, the contact film, and at least partially through the part being inspected thereby. The location sensor may sense and output information regarding how far the ultrasonic inspection system has traveled along the part. The processor may associate signals from the transducers with signals from the location sensor to determine precise locations on the part at which particular signals are received by the transducers.

17 Claims, 10 Drawing Sheets

(56) References Cited

U.S. PATENT DOCUMENTS

| | | | | |
|---|---|---|---|---|
| 4,672,852 | A * | 6/1987 | Gugel | G01N 29/265 376/245 |
| 5,494,038 | A * | 2/1996 | Wang | A61B 8/0866 600/459 |
| 5,549,004 | A * | 8/1996 | Nugent | G01N 29/2487 376/249 |
| 5,948,985 | A * | 9/1999 | Brautigan | G01N 29/223 73/622 |
| 5,969,255 | A * | 10/1999 | McLean | B21C 51/00 73/622 |
| 6,138,515 | A * | 10/2000 | Moufle | G01N 29/225 73/159 |
| 7,617,603 | B2 * | 11/2009 | Coleman | B23P 6/00 29/402.01 |
| 7,861,591 | B2 * | 1/2011 | Rath | G01N 29/221 73/577 |
| 7,975,549 | B2 * | 7/2011 | Fetzer | G01N 29/2468 73/626 |
| 8,746,070 | B2 * | 6/2014 | Tippit, Jr. | G01N 29/221 73/620 |
| 8,955,384 | B2 * | 2/2015 | Kleinert | G01N 29/043 73/627 |
| 9,360,461 | B2 * | 6/2016 | Na | G01N 29/28 |
| 9,915,632 | B2 * | 3/2018 | Owens | G01N 27/82 |
| 9,995,716 | B2 * | 6/2018 | Brignac | G01N 29/041 |
| 2004/0050167 | A1 * | 3/2004 | Linares | G01N 29/225 73/622 |
| 2004/0083815 | A1 * | 5/2004 | Lam | G01N 29/265 73/618 |
| 2005/0215901 | A1 * | 9/2005 | Anderson | A61B 8/12 600/445 |
| 2008/0066553 | A1 * | 3/2008 | Espada Tejedor | G01N 29/225 73/627 |
| 2012/0060609 | A1 * | 3/2012 | Fukutomi | G01N 29/225 73/592 |
| 2014/0260629 | A1 * | 9/2014 | Jaramillo | G01N 29/041 73/627 |
| 2016/0334374 | A1 * | 11/2016 | Koerner | G01N 29/28 |

\* cited by examiner

MODULAR FILM-COVERED ELASTOMERIC INSPECTION DEVICE

BACKGROUND

Commercial airplanes and components thereof are increasingly being manufactured from composite materials that may require ultrasonic inspection to determine part integrity. Inspections may be performed from one side (i.e., pulse-echo inspections) or from two sides, referred to herein as the through-transmission (TTU) methods. In either case, a transducer that transmits and/or receives sound waves must be acoustically coupled to the inspected part. Water or some other liquid is typically disposed between the transducer and the inspected part to provide a medium through which sound waves can travel. This can be accomplished by submerging the transducer and the part within a pool of water during inspection, but this method is inefficient and not practical for large parts.

Alternatively, a method known in the art as the "thin film" method may include a shoe surrounding the transducer and interfacing with the part to at least partially contain the water locally between the transducer and the part. However, because water leaks out between the shoe and the part, new water must be continuously pumped in to replace the water escaping. This method also requires that the escaping water be captured. Furthermore, when the surface of the inspected part is sharply contoured or roughly textured, the leakage rate may become so high that the water cannot be adequately contained long enough to maintain coupling.

In some alternative methods, a conformable solid or gel couplant is used to fill a gap between the part to be inspected and the transducer. For example, the gel may be Aqualene material by Olympus or Aquaflex by Parker Labs. However, these solid or gel couplants are not suitable for C-Scan inspections of sharply contoured or roughly textured composite parts, because they are too rigid to conform well to roughly textured surfaces and are easily damaged by sliding over roughly textured surfaces.

SUMMARY OF THE INVENTION

Embodiments of the present invention solve the above-mentioned problems and provide a distinct advance in the art of ultrasonic inspection.

One embodiment of the invention may include an ultrasonic inspection system for ultrasonic inspection of a part. The inspection system may include a transducer, an acoustic coupler made of an acoustic coupling compliant solid and fixed to a transmitting or receiving portion of the transducer, and a low friction contact film substantially surrounding the acoustic coupler or portions thereof. The transducer may transmit ultrasonic or sound waves through the acoustic coupler, the low friction contact film, and then at least partially through the part being inspected thereby.

In yet another embodiment of the invention, an ultrasonic inspection system for ultrasonic inspection of a part may include a handle, a handle bracket to which the handle is moveably and removably attached, a modular housing removably attached to the handle bracket, a contact film retainer removably attached to the modular housing, one or more transducers removably fixed to the modular housing, an acoustic coupler made of an acoustic coupling compliant solid and fixed relative to the one or more tranducers, a low friction contact film, a location sensor, and a processor. The low friction contact film may substantially surround the acoustic coupler or portions thereof extending outward of the modular housing. The transducer may transmit ultrasonic or sound waves through the acoustic coupler, the low friction contact film, and then at least partially through the part being inspected thereby. The location sensor may sense and output information regarding how far the ultrasonic inspection system has traveled along the part. The processor may associate signals from the transducer with signals from the location sensor to determine precise locations on the part at which particular signals are received by the at least one transducer.

According to another embodiment of the invention, a method for ultrasonic inspection of a part may include the steps of sliding a low friction contact film of an ultrasonic inspection system against a surface of the part and transmitting ultrasonic or sound waves from a transducer array through an acoustic coupler made of an acoustic coupling compliant solid and through the film to the part. Specifically, the film may be fixed to the transducer array with the acoustic coupler positioned between the film and the transducer array. Next, the method may include a step of receiving with the transducer array, or a secondary transducer array aligned on an opposing surface of the part, ultrasonic or sound waves reflected by or transmitted through the part. Then the method may include a step of determining one or more physical or structural characteristics or flaws of the part based on the ultrasonic or sound waves reflected by or transmitted through the part, as received by the transducer array or the secondary transducer array.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Figure 1:
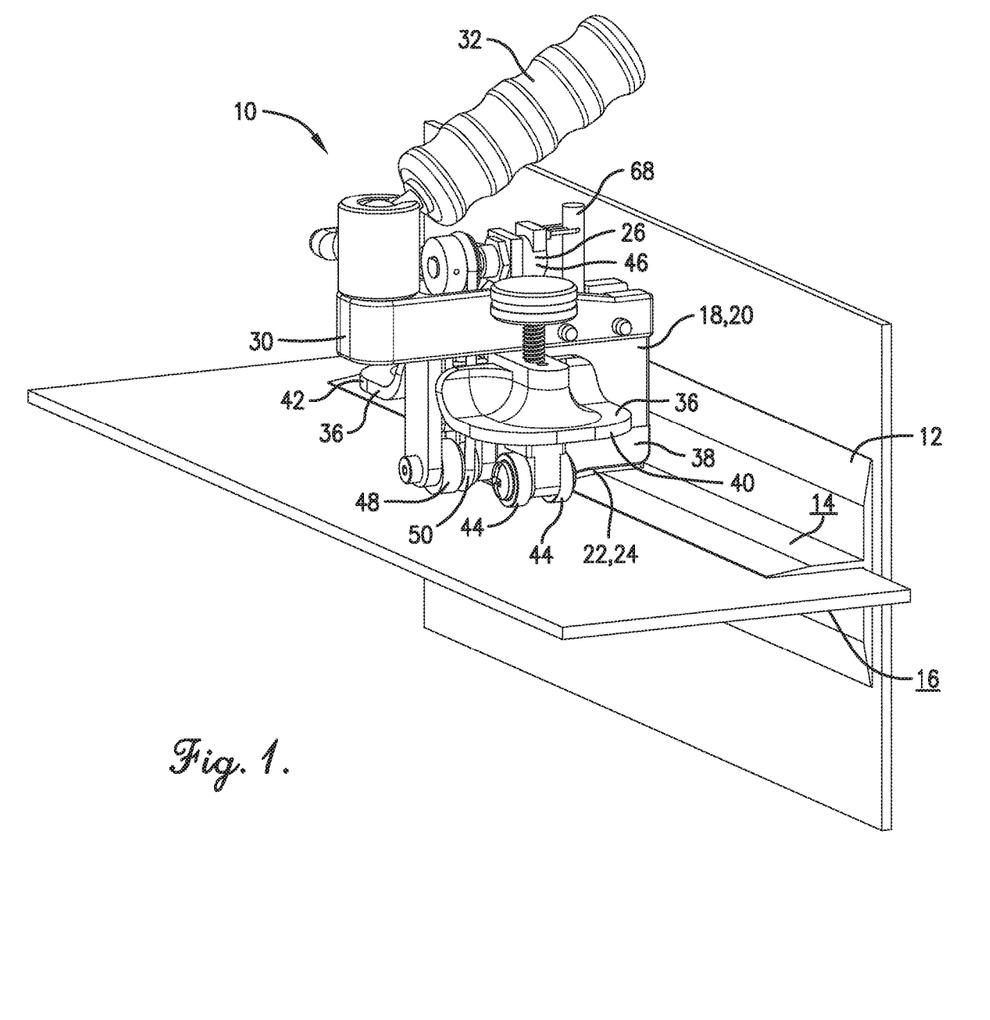
FIG. 1 is a front perspective view of an inspection system constructed according to embodiments of the present invention, placed on a part to be inspected.
Figure 2:
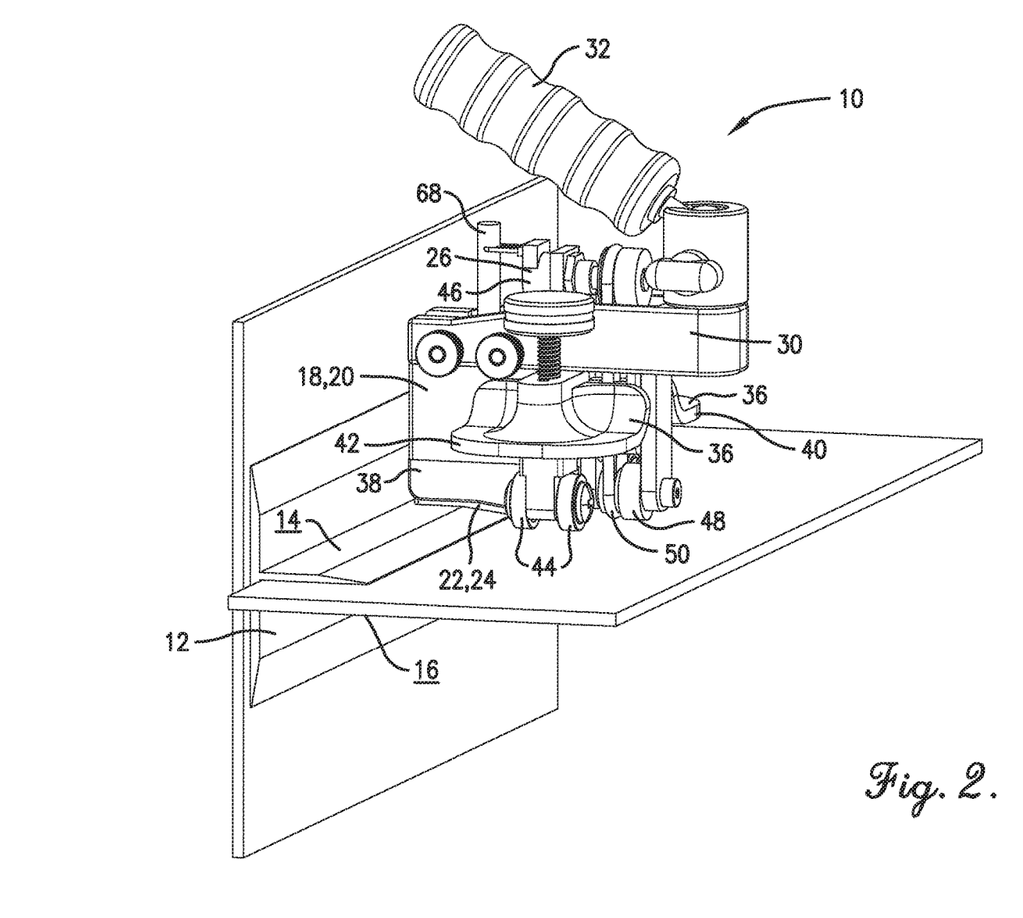
FIG. 2 is a back perspective view of the inspection system of FIG. 1 on the part.
Figure 3:
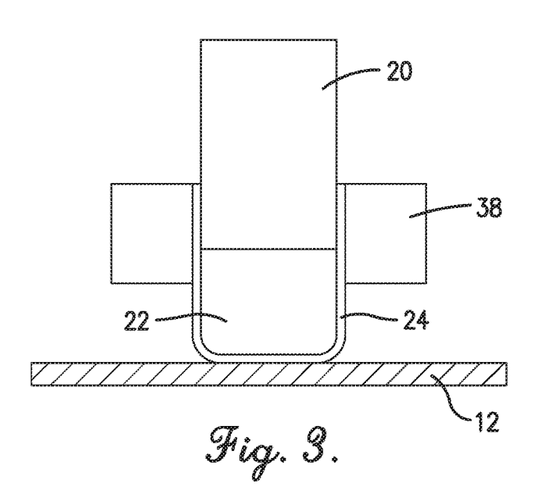
FIG. 3 is a cross-sectional schematic view of a transducer array, low friction contact film, and an acoustic coupler of the inspection system of FIG. 1, arranged in accordance with embodiments of the present invention.
Figure 4:
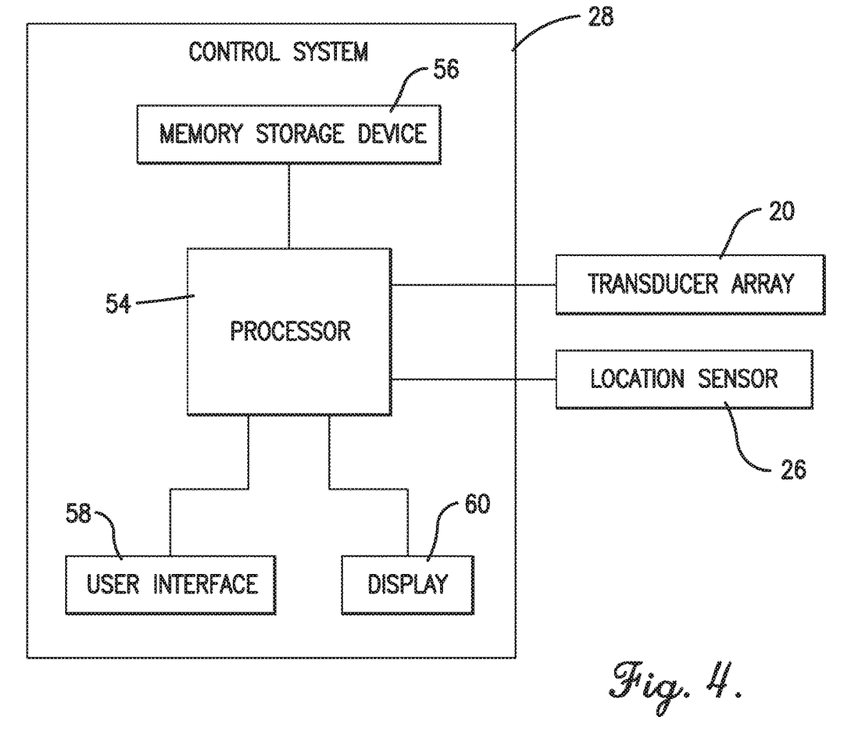
FIG. 4 is a block diagram of various components of the inspection system of FIG. 1 that are communicably coupled with each other.
Figure 5:
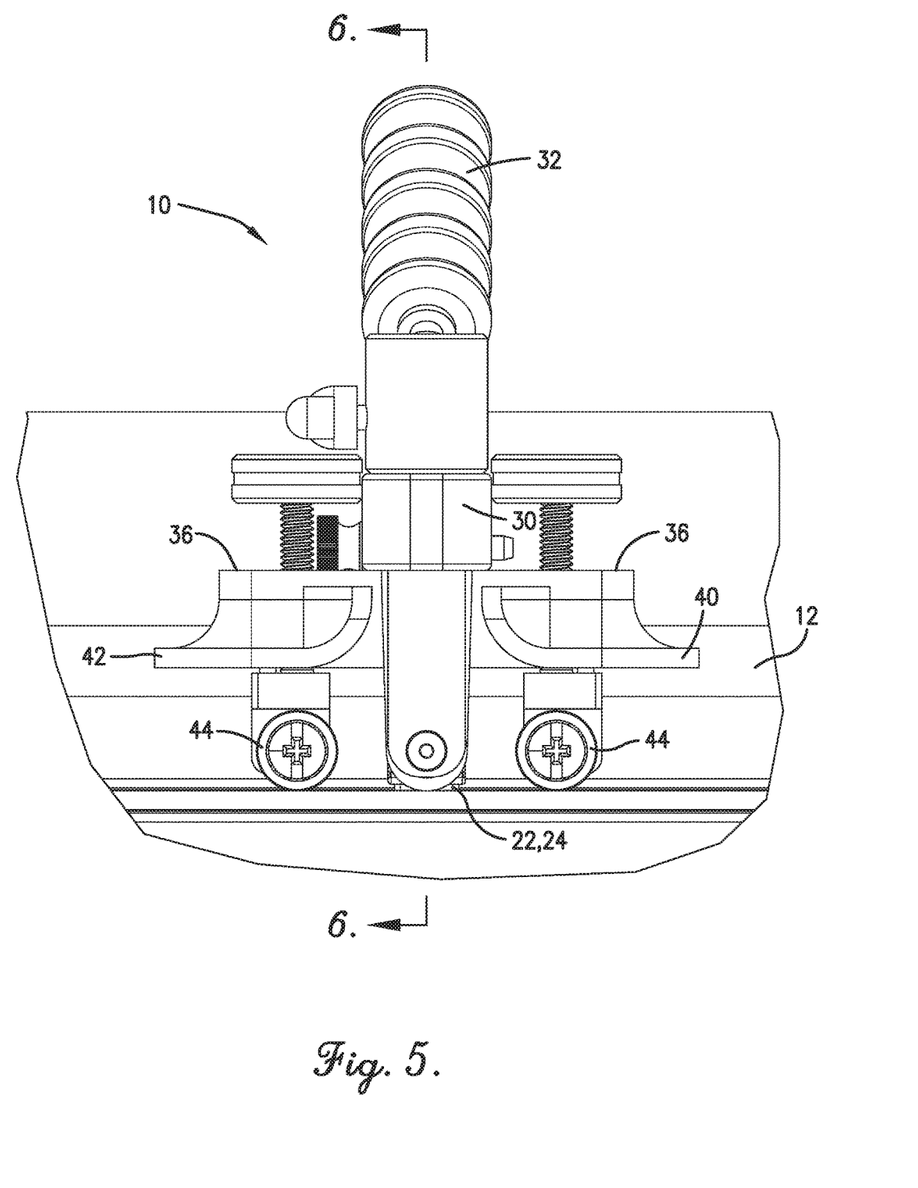
FIG. 5 is a side view of the inspection system of FIG. 1 on the part.

An inspection system 10 constructed in accordance with embodiments of the present invention is illustrated in FIGS. 1-3. The system 10 is configured for ultrasonic inspection of a part 12. The part 12 may be any component requiring ultrasonic inspection, such as an aircraft component, nacelle wall, honeycomb panel, and the like. The part 12 may have a first surface 14 and a second surface 16 opposite of the first surface 14. The part 12 may be of any shape or size and may include various contours, complex contours, corners, and the like. The system 10 may include at least one transducer or transducer array 20, an acoustic coupler 22 made of an acoustic coupling compliant solid, and a low friction contact film 24 substantially surrounding the acoustic coupler 22 or portions of the acoustic coupler 22. In some embodiments of the invention, as illustrated in FIG. 4, the inspection system 10 may also include a location sensor 26 and/or a control system 28.

As illustrated in FIGS. 1-2 and 5-10, components of the system may be modularly attached via a number of structural components and attachment devices, mechanically connected together, such that various components of the system 10 may be individually and/or independently removed and/or attached for replacement and/or for customization for a particular part or part shape. For example, the system 10 may further include a modular housing 18, a handle bracket 30 removeably attachable to the modular housing, a handle 32 moveably or removably attached to the handle bracket 30, and one or more outriggers 36 independently attachable to and removable from the modular housing 18. In some embodiments of the invention, the modular housing 18 may be used without the handle 32, handle bracket 30, and/or outriggers 36. In yet another embodiment of the invention, the modular housing 18 may be omitted entirely, with just the transducer array 20, acoustic coupler 22, and low friction contact film 24 being coupled as illustrated in FIG. 3, for example.

The modular housing 18 may be a housing for the transducer array 20, the low friction contact film 24, and/or the acoustic coupler 22. The modular housing 18 may also include or may be configured to function as a contact film retainer 38. The modular housing 18 or contact film retainer 38 may attach to and form a boundary around the transducer array 20 or a portion thereof and a portion of the acoustic coupler 22, thereby aiding in stabilizing the acoustic coupler 22. In some embodiments of the invention, the modular housing 18 and/or the contact film retainer 38 may be removably attached to the handle bracket 30.

The outriggers 36 may be mechanically, independently attachable and detachable from the modular housing 18 or other structural components of the system 10 and may be configured for maintaining normality of the transducer array 20 to a surface of the part 12. For example, the outriggers 36 may include a forward-protruding flange 40 and an aftward protruding flange 42, as well as a wheel 44 or wheels attached to the flanges 40, 42 and configured to rotate forward or aftward along one of the surfaces 14, 16 of the part 12 during inspection of the part 12.

The handle 32 may be configured to selectively pivot or rotate relative to the handle bracket 30 to which it is attached. This may allow the handle 32 to be repositioned to a desired angle or configuration as needed. Furthermore, in some embodiments of the invention, the handle 32 may be lockable in a selected configuration. The handle 32 may additionally or alternatively be detachable to provide clearance when needed for inspecting particular parts.

The transducer or transducer array 20 may include a plurality of transducers arranged in a linear array or any other pattern known in the art. For example, the transducer array 20 may comprise a plurality of transducers arranged in a plurality of rows and/or a plurality of columns. The transducer array 20 and/or the transducers thereof may be configured to transmit and/or receive ultrasonic or sound waves through the part 12. Specifically, the transducers and transducer array 20 may be defined herein as a device that senses and converts sound waves or ultrasonic waves into an electrical signal and/or converts electric signals into ultrasonic or soundwaves to emanate therefrom.

The low friction contact film 24 may comprise polytetrafluoroethylene (PTFE), fluorinated ethylene propylene (FEP), and/or polyethylene (PE). Other low friction films may be used without departing from the scope of the invention. The film 24 may be between 0.003 inches to 0.007 inches thick, or may have any thickness that does not unduly attenuate the ultrasonic or soundwaves passing therethrough.

The acoustic coupler 22 may be an acoustic coupling compliant solid and/or a low durometer solid couplant elastomer material. For example, the acoustic coupler 22 may be AQUAFLEX material available from Parker Laboratories, Inc. of Fairfield, N.J. or AQUALENE material available from Olympus Corporation of Tokyo, Japan. In some embodiments of the invention, the acoustic coupler 22 may be thick enough to allow it to conform to local, out-of-plane variations in contour of the part 12 without being unduly stressed. For example, if local, out-of-plane contour variations protruding one inch from a global surface contour are expected on surfaces of the part 12, three inches of minimal thickness of the acoustic coupler 22 may ensure that no part of the acoustic coupler 22 is compressed more than 33-percent from its nominal thickness when brought into contact with those part surfaces 14,16.

In some embodiments of the invention, the acoustic coupler 22 may have a thickness in a range of 0.2 inches to 0.8 inches uncompressed. For example, the acoustic coupler 22 may have a thickness of approximately 0.5 inches and a width of approximately 0.5 inches. The modular housing 18 or contact film retainer 38 may surround a point at which the transducer array 20 meets the acoustic coupler 22, and the modular housing 18 or contact film retainer 38 may extend to overlap approximately half a thickness of the acoustic coupler 22. However, other dimensions may be used without departing from the scope of the invention.

Figure 6:
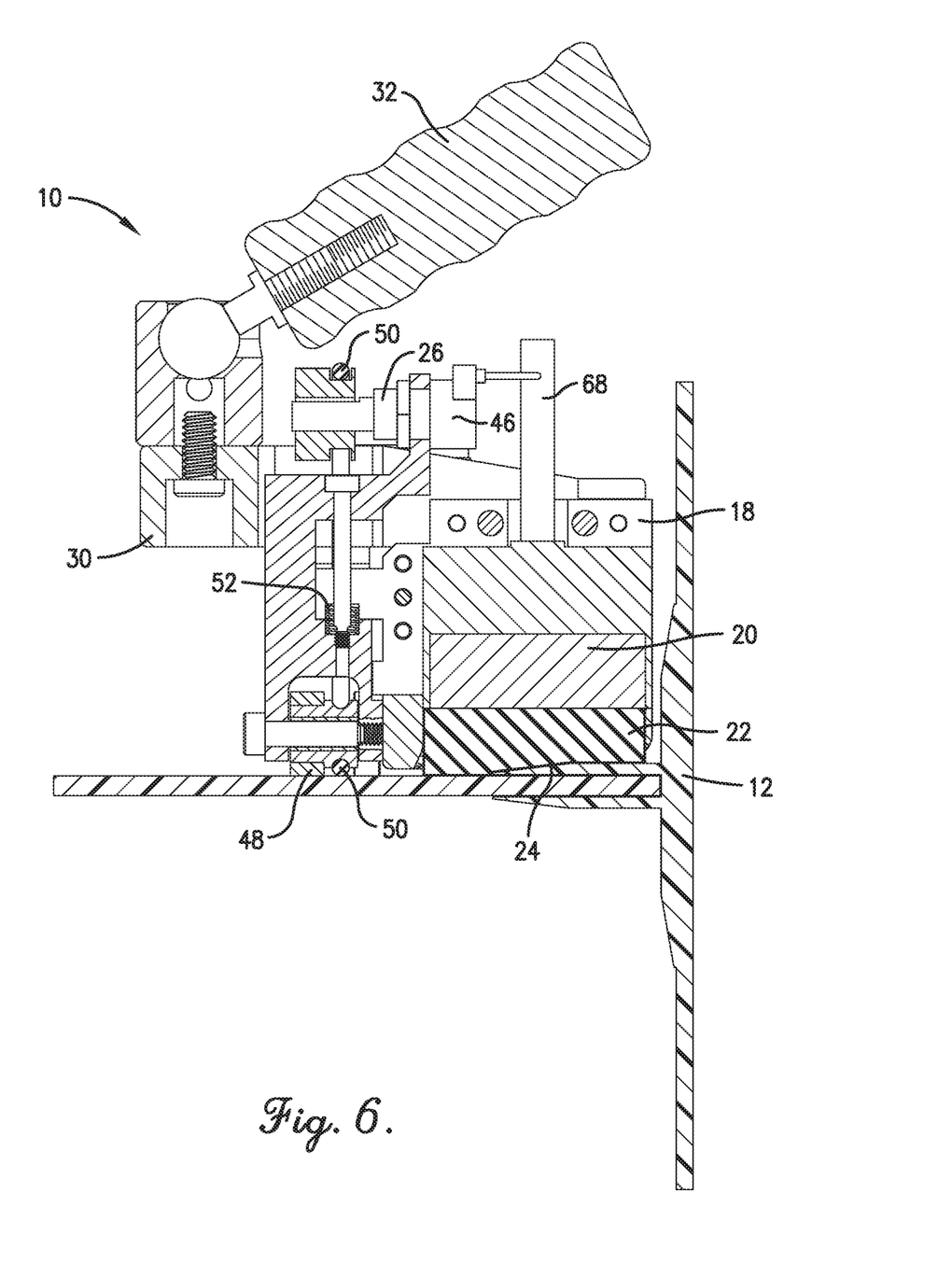
FIG. 6 is a cross-sectional view of the inspection system of FIG. 5 on the part, taken along line 6-6.

The location sensor 26 may be configured to sense and output information regarding how far the inspection system 10 has traveled along the part 12. In some embodiments of the invention, the location sensor 26 may include a rotary encoder 46. Other components of the location sensor 26 may include an engagement wheel 48, an elastic belt 50, and a resilient member 52, as illustrated in FIG. 6. For example, the rotary encoder 46 and/or the engagement wheel 48 may be spring-biased and configured to provide location information regarding a distance the ultrasonic inspection system 10 has traveled along the part 12. The rotary encoder 46 may be rotatably driven by motion of the engagement wheel 48 against one of the surfaces 14,16 of the part 12, via the elastic belt 50 or other rotary coupling mechanisms and configurations. The rotary encoder 46 may also be communicably coupled with control system 28, such as via communication cables 68 or wires, to provide information thereto regarding a distance traveled by the inspection system 10 along the part 12. The resilient member 52 may serve as shocks for the engagement wheel 48, such that small deviations in the surface 14,16 of the part 12 will not affect the readings provided by the rotary encoder 46 rotatably coupled to the engagement wheel 48 via the elastic belt 50, as illustrated in FIGS. 6-10.

The resilient member 52 may be a spring, shocks, hydraulic shocks, or any resilient member known in the art for compressing or expanding when a sufficient force is supplied thereto, but automatically returning to a naturally-biased position or naturally-biased state once force is removed therefrom. In some alternative embodiments of the invention, the resilient member 52 may comprise a pressure regulator, gas pressure source, and/or fluid pressure source fluidly coupled with the rotary encoder 46 and/or engagement wheel 48 in such a manner as to urge the rotary encoder 46 and/or engagement wheel 48 toward the part 12.

In some embodiments of the invention, at least some of the actuation of the modular housing 18 may be controlled by a programmed processor, microcontroller, related circuitry, and the like. For example, actuation and support components such as rails, motors, controllers, and/or various electrical and communication elements may be used for properly locating and actuating travel of the inspection system 10 relative to the part 12. However, manual actuation of the inspection system 10 may be used without departing from the scope of the invention. Data received by the transducer array 20 may also be sent to a programmed processor, microcontroller, related circuitry, memory, databases, cloud storage devices, and the like. For example, the transducer array 20 and the location sensor 26 may be electrically and/or communicably coupled with the control system 28.

Figure 11:
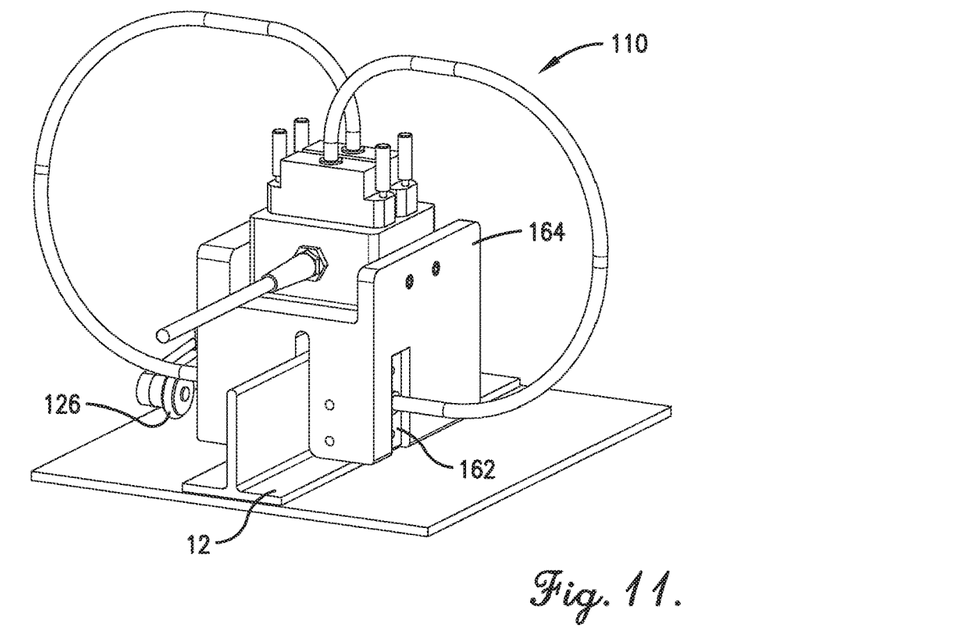
FIG. 11 is a front perspective view of an inspection system, constructed in accordance with an alternative embodiment of the invention, and having two transducers on opposing sides of a part to be inspected.
Figure 12:
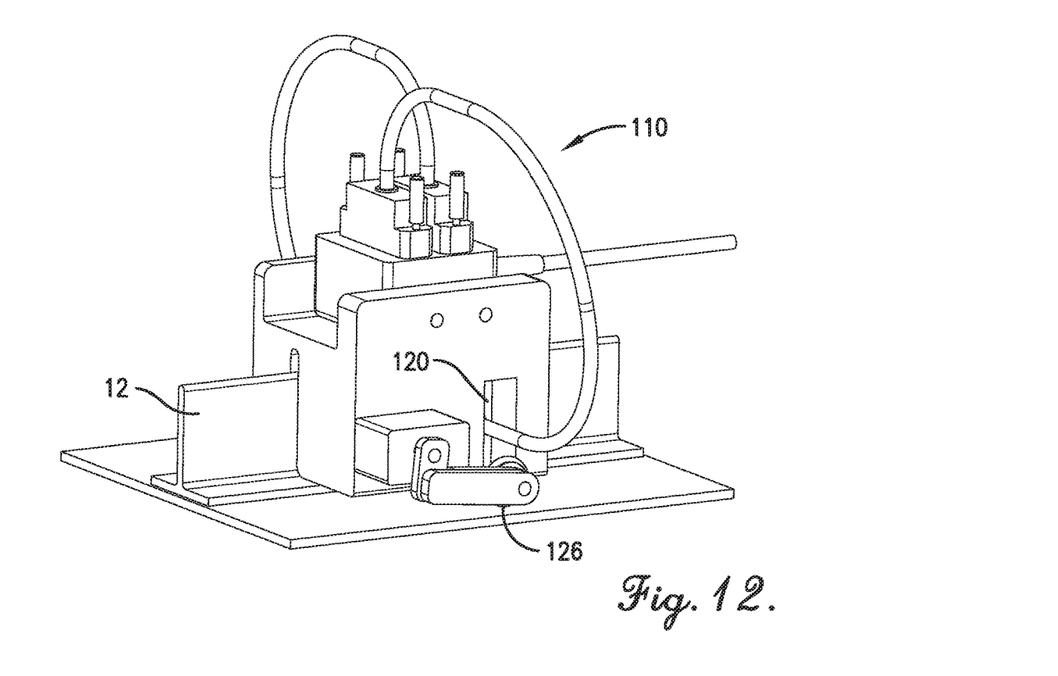
FIG. 12 is a side perspective view of the inspection system of FIG. 11.
Figure 13:
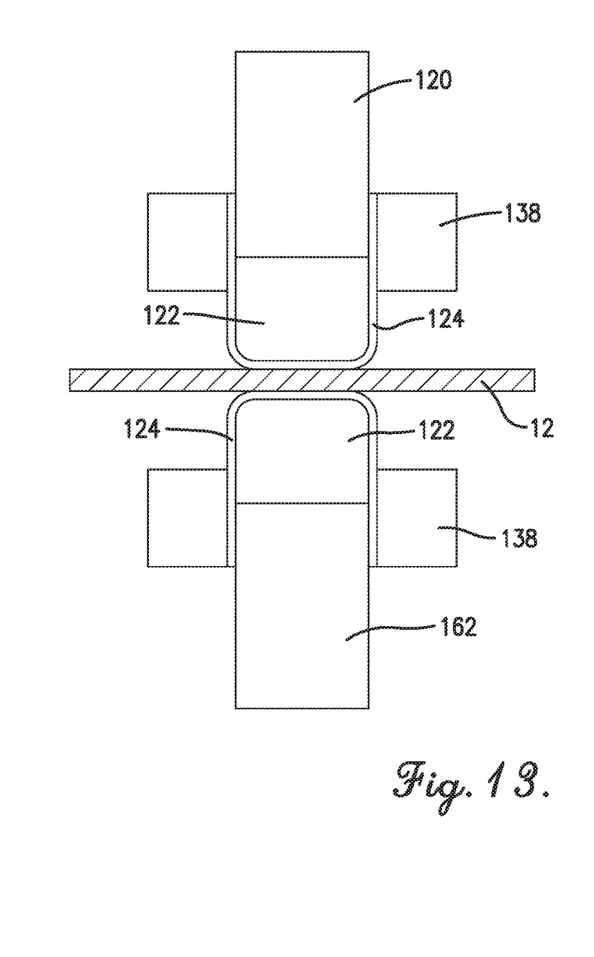
FIG. 13 is a cross-sectional schematic view of two transducer arrays of the inspection system of FIG. 11, facing each other on opposing sides of the part to be inspected.

As illustrated in FIG. 4, the control system 28 may include a processor 54, a memory storage device 56, a user interface 58, and/or a display 60 and may be communicably coupled with the transducer array 20, the location sensor 26, and/or a secondary transducer array 162 (as illustrated in FIGS. 11-13 and later described herein) or other sensors. For example, the control system 28 may be configured to associate signals from the transducer array 20 with signals from the location sensor 26 to determine precise locations on the part 12 at which particular signals are received by the transducer array 20.

The control system 28 and/or the processor 54 thereof may include any computer or processor known in the art and may further include any number and combination of controllers, circuits, integrated circuits, programmable logic devices such as programmable logic controllers (PLC) or motion programmable logic controllers (MPLC), microcontrollers, other electrical and computing devices, and/or other data and signal processing devices for carrying out the functions described herein, and may additionally comprise one or more memory storage devices, transmitters, receivers, and/or communication busses and ports. In some embodiments of the invention, the processor 54 may comprise several separate processors or computing devices which may communicate and exchange information with each other and may even be located in remote locations relative to each other.

The control system 28 or processor 54 thereof may be configured to implement any combination of the algorithms, subroutines, or code corresponding to method steps and functions described herein. The control system 28 or processor 54 and computer programs described herein are merely examples of computer equipment and programs that may be used to implement the present invention and may be replaced with or supplemented with other computers, processors, and/or computer programs without departing from the scope of the present invention. While certain features are described as residing in the processor 54 or control systems associated therewith, the invention is not so limited, and those features may be implemented elsewhere.

In various embodiments of the invention, the control system 28 or processor 54 thereof may implement a computer program and/or code segments to perform some of the functions described herein. The computer program may comprise an ordered listing of executable instructions for implementing logical functions in the processor. For example, the computer program may be a software program configured to run on a computer, such as a personal computer, laptop, tablet, or the like. The computer program can be embodied in any computer-readable medium for use by or in connection with an instruction execution system, apparatus, or device, and execute the instructions. In the context of this application, a "computer-readable medium" can be any physical means that can contain, store, communicate, propagate, or transport the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), a portable compact disk read-only memory (CDROM), an optical fiber, multi-media card (MMC), reduced-size multi-media card (RS MMC), secure digital (SD) cards such as microSD or miniSD, and a subscriber identity module (SIM) card.

As noted above, the control system 28 may comprise memory storage devices 56 or other various memory elements. The memory storage devices 56 may be integral with the control system, stand-alone memory, or a combination of both. The memory storage devices may include, for example, removable and non removable memory elements such as RAM, ROM, flash, magnetic, optical, USB memory devices, MMC cards, RS MMC cards, SD cards such as microSD or miniSD, SIM cards, and/or other memory elements.

The user interface 58 may comprise a mouse, keyboard, touch screen, switches, buttons, or various data input ports whereby the user may input data directly into the control system or otherwise exchange information with the control system 28 or its associated components. In some embodiments of the invention, the user interface 58 may also include a power switch or the like for turning on power to the system 10.

The display 60 or display screen of the control system 28 may be configured for providing visual graphics, text instructions, and other information to a user or operator. The display 60 may be communicably coupled with the processor 54 and may include a plurality of displays. The display 60 may be, for example, a cathode ray tube (CRT), a liquid crystal display (LCD), a light emitting diode (LED) display, or the like. In some embodiments of the invention, the display 60 or displays may be touch screens serving as an integrated display and user interface in one.

The inspection system 10 described herein may be used for one-sided inspections of the part 12. For two-sided or TTU inspections of the part 12, an inspection system 110, having many identical components to the inspection 10, may be used. However, the inspection system 110 may additionally include the secondary transducer array 162, as illustrated in FIGS. 11-13, aligned on an opposite side of the part 12 from a transducer array 120, also referred to herein as the primary transducer array 120. The primary transducer array 120 may be substantially identical to the transducer array 20 described above, and may likewise couple with an acoustic coupler 122, a low friction contact film 124, and a contact film retainer 138, each substantially identical to the acoustic coupler 22, the low friction contact film 24, and the contact film retainer 38, respectively.

In this alternative embodiment of the invention illustrated in FIGS. 11-13, the primary transducer array 120 and the secondary transducer array 162 may be fixed in facing linear alignment with each other, using a positioning frame or housing 164. The distance between the secondary transducer array 162 and the primary transducer array 120 may be fixed or may be adjustable via mechanical adjusting or attachment components (not shown). The inspection system 110 may also include position sensors 126 similar to identical to the position sensor 26 described above, and/or other components of the inspection system 10 described above without departing from the scope of the invention. Likewise, one or more components of the inspection system 110 may be modular and/or detachable for part replacement, repair, or clearance accommodations.

In use, a method for ultrasonic inspection may include sliding the low friction contact film 24 of the inspection system 10 against one of the surfaces 14,16 of the part 12, sending ultrasonic or sound waves from the transducer array 20 to the part 12. These waves will then reflect back to and be sensed by the transducer array 20 or travel through the part 12 and be received by the secondary transducer array 162 on an opposite side of the part 12. These signals received by the transducer array 20 and/or the secondary transducer array 162 may be interpreted by the control system 28 and/or associated with signals from the location sensor 26 to determine physical characteristics of the part 12 at specific locations on the part 12 being inspected.

Figure 14:
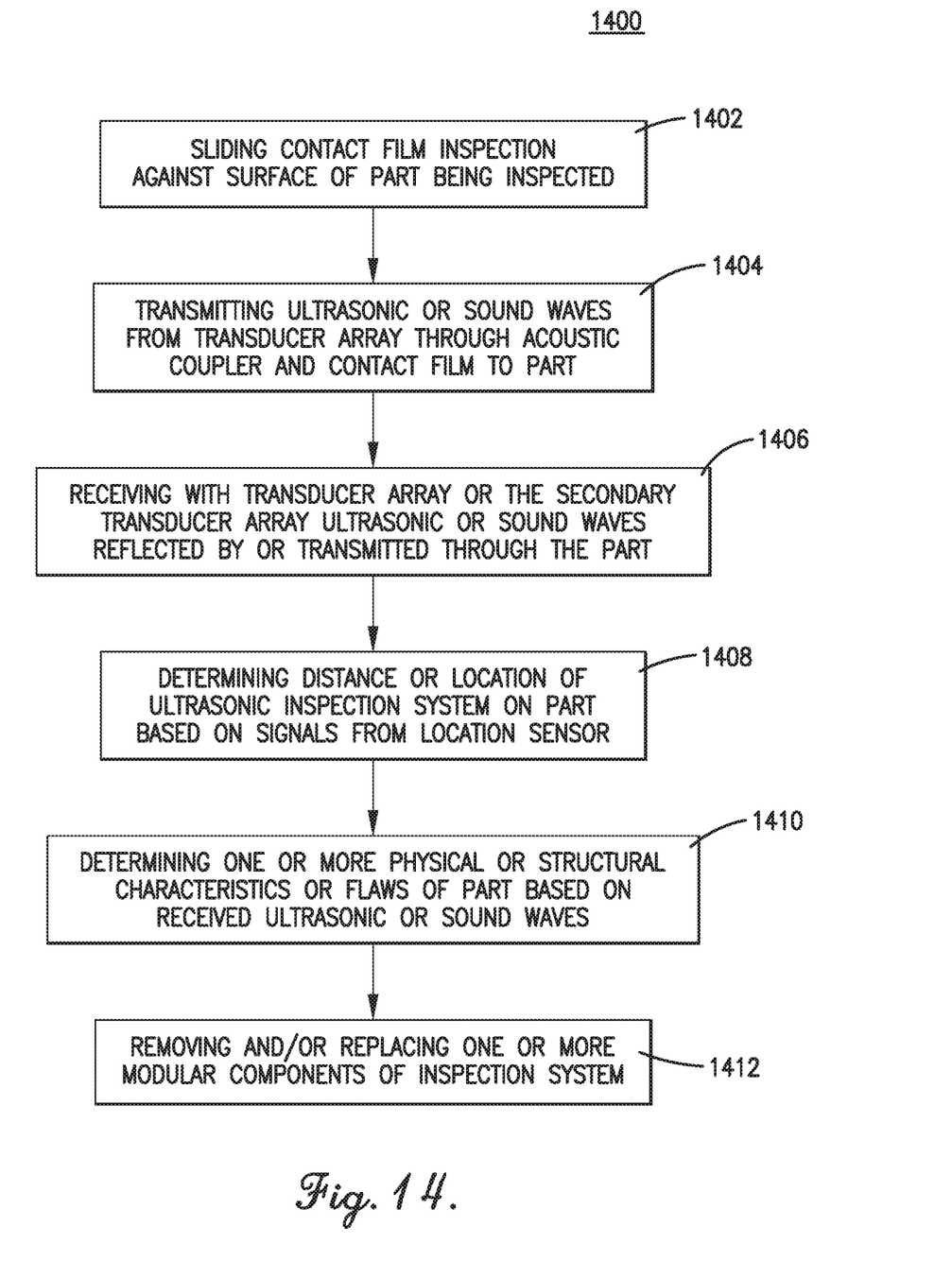
FIG. 14 is a flow chart illustrating a method of performing ultrasonic inspection of a part in accordance with embodiments of the present invention.

Method steps for ultrasonic inspection will now be described in more detail, in accordance with various embodiments of the present invention. The steps of the method 1400 may be performed in the order as shown in FIG. 14, or they may be performed in a different order. Furthermore, some steps may be performed concurrently as opposed to sequentially. In addition, some steps may not be performed.

The method 1400 for ultrasonic inspection of the part 12, as illustrated in FIG. 14, may include a step of sliding the low friction contact film 24 of the inspection system against a surface of the part 12, as depicted in block 1402. As described above and illustrated herein, the film 24 is fixed to the transducer array 20 with the acoustic coupler 22 positioned between the film 24 and the transducer array 20.

Next, the method 1400 may include a step of transmitting ultrasonic or sound waves from the transducer array 20 through the acoustic coupler 22 and the film 24 to the part 12, as depicted in block 1404, and then receiving with the transducer array 20, or the secondary transducer array 162, ultrasonic or sound waves reflected by or transmitted through the part 12, as depicted in block 1406. For example, in some embodiments of the invention, such as for pulse-echo inspection of the part 12, the transducer array 20 may both send the ultrasonic or sound waves as well as receive the reflected ultrasonic or sound waves, as reflected off of the part 12. In other embodiments of the invention, as illustrated in FIGS. 11-13, as when TTU inspection is performed, the secondary transducer array 162 aligned on an opposing surface of the part 12 may receive whatever portion of the ultrasonic or sound waves travel through the part 12 from the primary transducer array 120.

In some embodiments of the invention, the method 1400 may further comprise a step of determining a distance or location of the ultrasonic inspection system 10 on the part 12 based on signals from the location sensor 26, as depicted in block 1408. For example, as noted above, the rotary encoder 46, and/or the engagement wheel 48 rotatably coupled with the rotary encoder 46, may be configured and positioned to naturally rotate along the surface 14,16 of the part 12 during the step of sliding the low friction contact film 24 against the surface 14,16 of the part 12. Thus, signals from the rotary encoder may be transmitted to the control system 28 for analysis.

The method 1400 may then include a step of determining one or more physical or structural characteristics or flaws of the part 12 based on the ultrasonic or sound waves reflected by or transmitted through the part 12, as depicted in block 1410. This step may also include determining locations on the part 12 of these characteristics or flaws based on signals received from the location sensor 26. For example, by corresponding signals from the rotary encoder 46 with the signals received by the transducer array 20 or secondary transducer array 162, the control system 28 may create a database and/or map of various physical or structural characteristics or flaws of the part 12. This map or values associated therewith may be, for example, provided to a user on the display 60 of the control system 28.

Figure 7:
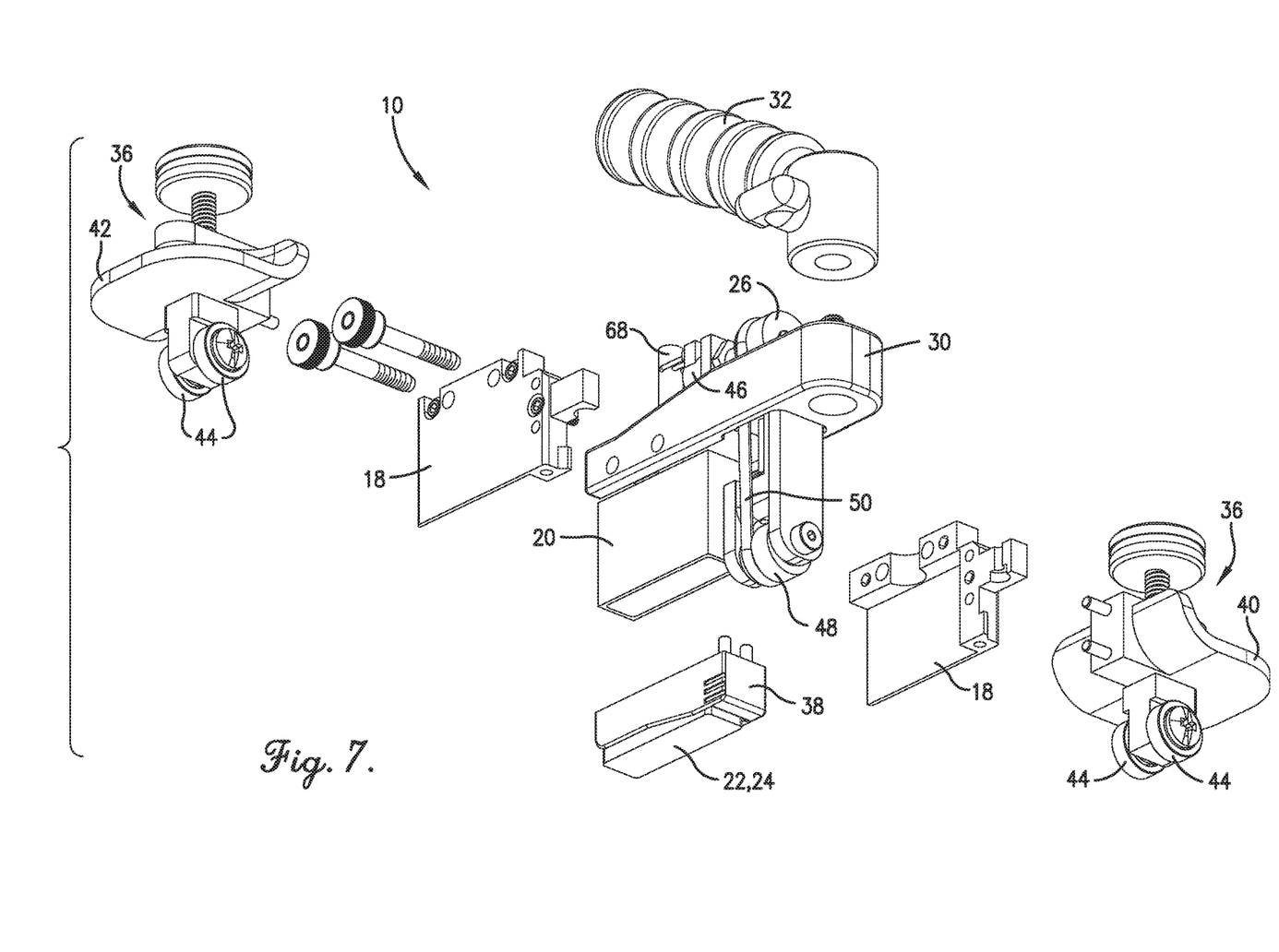
FIG. 7 is an exploded perspective view of the inspection system of FIG. 1, illustrating detachability of these components.
Figure 8:
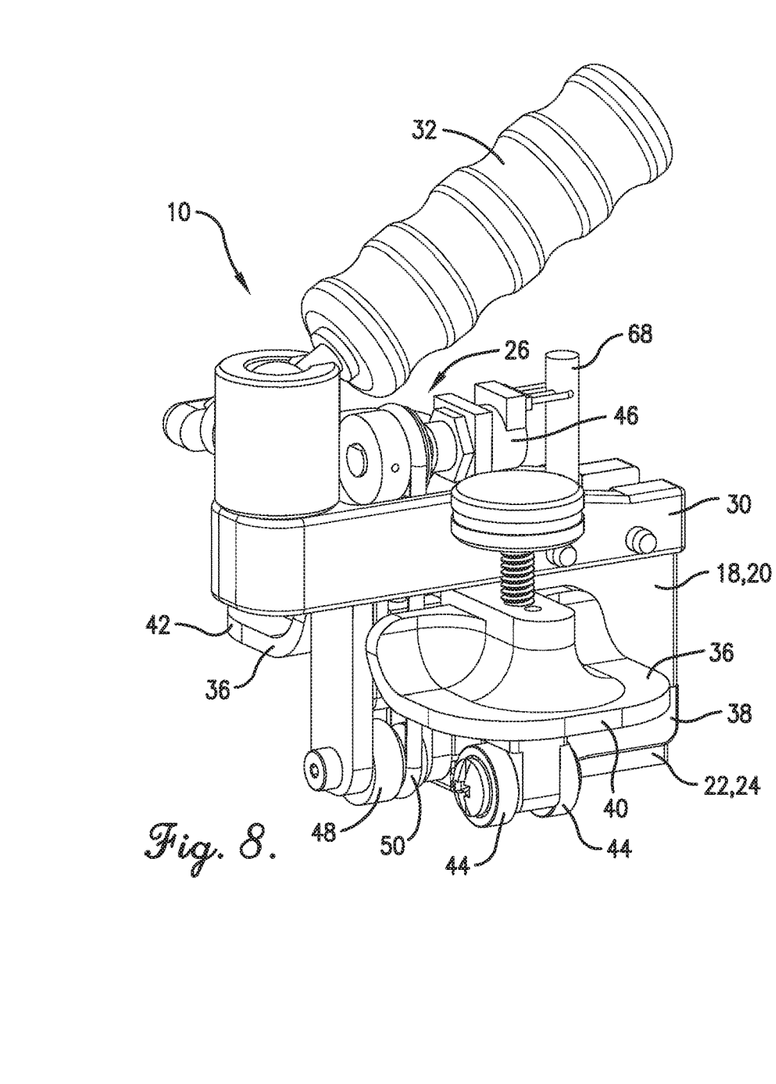
FIG. 8 is a front perspective view of the inspection system of FIG. 1.
Figure 9:
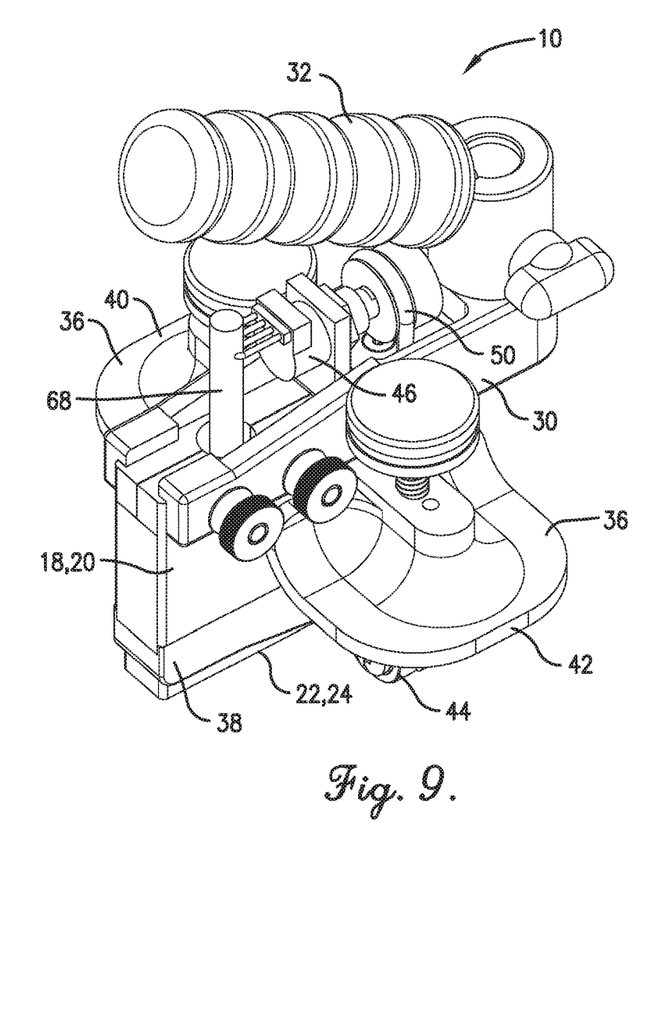
FIG. 9 is a back perspective view of the inspection system of FIG. 1.
Figure 10:
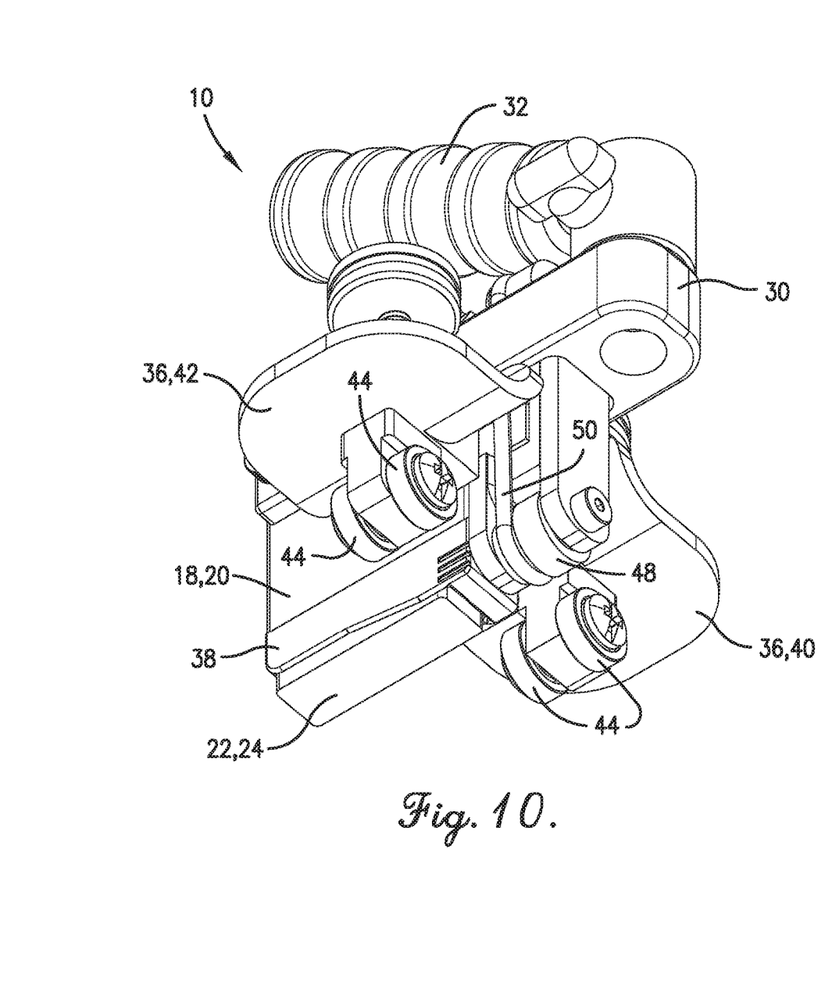
FIG. 10 is a bottom perspective view of the inspection system of FIG. 1.

In some embodiments of the invention, the method 1400 may additional include steps of removing and/or replacing one or more modular components of the inspection system 10, as depicted in block 1412. For example, as described above and illustrated in FIG. 7, one or both of the outriggers 36 may be independently removed from the modular housing 18 via mechanical fasteners or the like in order to create sufficient clearance to accommodate a particular part's configuration and/or in order to replace the outriggers 36 with new or different outriggers. Furthermore, the modular housing 18 and/or the contact film retainer 38 described above may be easily removed or separated via mechanical fasteners, as illustrated in FIG. 7, particularly if the transducer array 20, film 24, or acoustic coupler 22 is damaged or worn and requires replacement.

Advantageously, the inspection system 10 and methods described herein allow inspection of sharply contoured or roughly textured composite surfaces by means of sliding contact. Furthermore, the modular nature and adjustability of various components of the inspection system 10 described herein allows for the inspection of a wide variety of parts.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An ultrasonic inspection system for ultrasonic inspection of a part having a surface, the system comprising:
    at least one transducer, wherein the at least one transducer is configured to transmit ultrasonic or sound waves through the part;
    an acoustic coupler made of an acoustic coupling compliant solid and fixed to a transmitting or a receiving portion of the transducer;
    a low friction contact film substantially surrounding the acoustic coupler or portions of the acoustic coupler; and
    an outrigger configured to be rigidly coupled to the at least one transducer so as to maintain normality of the at least one transducer to the surface of the part such that the at least one transducer transmits ultrasonic or sound waves through the part at an angle normal to the surface of the part, the outrigger being independently removable from the at least one transducer for accommodating a shape of the part.

2. The system of claim 1, further comprising a modular housing attachable to the transducer and a contact film retainer attached to the modular housing.

3. The system of claim 1, further comprising structure forming a boundary around at least a portion of the acoustic coupler for stabilizing the acoustic coupler.

4. The system of claim 1, wherein the outrigger comprises wheels configured to rotate forward or aftward along the surface of the part during inspection of the part.

5. The system of claim 2, further comprising a handle and a handle bracket attachable to the modular housing, wherein the handle is at least one of removeably, rotatably, and pivotally attached to the handle bracket.

6. The system of claim 1, wherein the low friction contact film comprises at least one of polytetrafluoroethylene (PTFE), fluorinated ethylene propylene (FEP), and polyethylene (PE).

7. The system of claim 1, wherein the acoustic coupling compliant solid is a low durometer solid couplant elastomer material.

8. The system of claim 1, wherein the at least one transducer includes a linear array of transducers configured to at least one of send and receive ultrasonic waves through the part.

9. The system of claim 1, further comprising a rotary encoder rotatably coupled with a resilient member and configured to provide location information regarding a distance the ultrasonic inspection system has traveled along the part.

10. An ultrasonic inspection system for ultrasonic inspection of a part having a surface, the system comprising:
    at least one transducer configured to transmit ultrasonic or sound waves through the part;
    an acoustic coupler made of an acoustic coupling compliant solid and fixed to the transducer;
    a low friction contact film substantially surrounding the acoustic coupler or portions of the acoustic coupler;
    a location sensor configured to sense and output information regarding how far the ultrasonic inspection system has traveled along the part;
    a processor configured to associate signals from the at least one transducer with signals from the location sensor to determine precise locations on the part at which particular signals are received by the at least one transducer; and
    an outrigger configured to be rigidly coupled to the at least one transducer so as to maintain normality of the at least one transducer to the surface of the part such that the at least one transducer transmits ultrasonic or sound waves through the part at an angle normal to the surface of the part, the outrigger being independently removable from the at least one transducer for accommodating a shape of the part.

11. The system of claim 10, further comprising structure forming a boundary around at least a portion of the acoustic coupler for stabilizing the acoustic coupler.

12. The system of claim 10, wherein the low friction contact film comprises at least one of polytetrafluoroethylene (PTFE), fluorinated ethylene propylene (FEP), and polyethylene (PE).

13. The system of claim 10, wherein the acoustic coupling compliant solid is a low durometer solid couplant elastomer material.

14. The system of claim 10, wherein the at least one transducer includes a linear array of transducers configured to at least one of send and receive ultrasonic waves through the part.

15. The system of claim 10, wherein the location sensor includes a rotary encoder and a spring-biased engagement wheel rotatably coupled with the rotary encoder, wherein the engagement wheel is configured to freely roll along a surface of the part as the low-friction contact film is slid along the surface of the part, wherein the rotary encoder is actuated to rotate by rotation of the engagement wheel and is configured to provide location information regarding a distance the ultrasonic inspection system has traveled along the part.

16. A method for ultrasonic inspection of a part having a surface, the method comprising the steps of:
- sliding a low friction contact film of an ultrasonic inspection system against a surface of the part, wherein the film is fixed to a transducer with an acoustic coupler made of an acoustic coupling compliant solid and positioned between the film and the transducer;
- transmitting ultrasonic or sound waves from the transducer through the acoustic coupler and the film to the part;
- receiving with the transducer, or a secondary transducer aligned on an opposing surface of the part, ultrasonic or sound waves reflected by or transmitted through the part;
- determining one or more physical or structural characteristics or flaws of the part based on the ultrasonic or sound waves reflected by or transmitted through the part;
- maintaining normality of the transducer to the surface of the part via an outrigger rigidly coupled to the transducer such that the transducer transmits the ultrasonic or sound waves through the part at an angle normal to the surface of the part; and
- independently removing the outrigger from the transducer for accommodating a shape of the part.

17. The method of claim 16, wherein the ultrasonic inspection system further includes a rotary encoder having a spring-biased attachment to a frame or a housing of the ultrasonic inspection system, wherein the rotary encoder is positioned to naturally rotate along the surface of the part during the step of sliding the low friction contact film against the surface of the part, wherein the method further comprises determining a distance or location of the ultrasonic inspection system on the part based on signals from the rotary encoder.

* * * * *